United States Patent
Long et al.

(10) Patent No.: US 9,598,344 B2
(45) Date of Patent: Mar. 21, 2017

(54) β-HYDROXY-β-METHYLBUTYRIC (HMB) ACID PURIFICATION METHOD

(71) Applicants: TSI (China) Co, LTD, Shanghai (CN); TSI Pharmaceutical (Ji-Angyin) Co., LTD, Jiangsu (CN)

(72) Inventors: Ling Long, Shanghia (CN); Yongehun Tang, Jiangsu (CN)

(*) Notice: Subject to any disclaimer, the term of this patent is extended or adjusted under 35 U.S.C. 154(b) by 0 days.

(21) Appl. No.: 14/783,949

(22) PCT Filed: Dec. 6, 2013

(86) PCT No.: PCT/CN2013/088762
§ 371 (c)(1),
(2) Date: Oct. 12, 2015

(87) PCT Pub. No.: WO2014/166273
PCT Pub. Date: Oct. 16, 2014

(65) Prior Publication Data
US 2016/0052856 A1    Feb. 25, 2016

(30) Foreign Application Priority Data
Apr. 12, 2013    (CN) .......................... 2013 1 0127262

(51) Int. Cl.
C07C 51/42    (2006.01)
C07C 51/29    (2006.01)

(52) U.S. Cl.
CPC .............. C07C 51/42 (2013.01); C07C 51/29 (2013.01)

(58) Field of Classification Search
None
See application file for complete search history.

(56) References Cited

U.S. PATENT DOCUMENTS

| 3,228,963 A | * | 1/1966 | Joo | ......................... C07C 51/48 208/18 |
| 4,992,470 A | | 2/1991 | Nissen | |
| 6,090,978 A | | 7/2000 | McCoy | |

FOREIGN PATENT DOCUMENTS

| CN | 1417190 | 5/2003 |
| CN | 102911085 | 2/2013 |
| WO | 2013025775 | 2/2013 |

OTHER PUBLICATIONS

Sulpizio "Advances in Filter aid and Precoat Filtration Technology", Presentation at the American Filtration & Separations Society Apr. 6-9, 1999.*

* cited by examiner

Primary Examiner — Sudhakar Katakam
Assistant Examiner — Ana Z Muresan
(74) Attorney, Agent, or Firm — Davis, Brown, Koehn, Shors & Roberts, P.C.

(57) ABSTRACT

The present invention relates generally to the field of chemical synthesis. Specifically, the present invention relates to a method for purification of β-hydroxyl-β-methyl butyrate comprising (1) neutralizing a crude β-hydroxyl-β-methyl butyrate; (2) cooling and crystallizing the crude β-hydroxyl-β-methyl butyrate solution to create a β-hydroxyl-β-methyl butyrate salt; (3) dissolving and acidifying the salt; and (4) extracting the resultant high purity β-hydroxyl-β-methyl butyrate. Additionally, the present invention relates to a method of obtaining high purity β-hydroxyl-β-methyl butyrate at normal temperature and vacuum conditions.

13 Claims, No Drawings

β-HYDROXY-β-METHYLBUTYRIC (HMB) ACID PURIFICATION METHOD

CROSS-REFERENCE TO RELATED APPLICATION(S)

This application claims priority under 35 U.S.C. 371 to International Patent Cooperation Treaty Application Serial No. PCT/CN2013/088762 filed Dec. 6, 2013 and to Chinese Application No. CN 201310127262 filed Apr. 12, 2013, and incorporates the same herein in its entirety by this reference.

TECHNICAL FIELD

The present invention relates to the field of chemical synthesis. Specifically, the present invention relates to a method for purification of β-hydroxyl-β-methyl butyrate.

TECHNICAL BACKGROUND

β-hydroxyl-β-methyl butyrate (HMB, $C_5H_{10}O_3$) is an intermediate metabolite of leucine, which is a kind of essential amino acid. Leucine is a branched amino acid and is essential. It is not produced in vivo, but it is very important to the human health. People have to rely on diet to ensure sufficient intake of leucine. Similar to leucine, HMB is contained in food, and the human body can also produce a small amount of HMB.

Currently a monohydrate of the calcium salt of HMB is being marketed in the health product industry. Although the metabolic mechanism humans use to produce HMB in vivo is unclear, the compound has been recommended for use against muscle protein degradation during resistive exercise. Additionally, HMB can facilitate the increase of muscle volume. Researchers have proposed that HMB might be essential to the muscle cell membrane during exercise stress, or alternatively that it may regulate activity of some enzymes which are important for muscle growth. Tests on non-human subjects have shown that supplementing HMB may increase fat-free body weight and reduce body fat.

Methods for synthesizing HMB are well-known in the industry. However, it is somewhat difficult to obtain high purity HMB. Current methods for HMB purification include distillation or repetitious extraction and washing.

Because HMB is prone to produce impurities at high temperatures, distillation must be carried out rapidly and at a reduced pressure of about 40 mmHg and because the temperature is about 120° C. HMB purification by distillation also places strain on processing equipment because the process must be operated at high temperature and high vacuum, and the equipment must be resistant to corrosion by acid and chloride ions. As a result, it is difficult to find equipment to satisfy the processing requirements. Additionally, distillation creates a front cut fraction and cauldron bottom residue in addition to the desired HMB product. If the front cut fraction and cauldron bottom residue are utilized, the distillation process is not be cost-effective. Equipment strain, high cost, and by-product production are all downsides of the distillation method for purification.

In the repetitious extraction and washing method, HMB is purified by multiple extractions and reverse extractions by utilizing different partition ratios of HMB and impurities in water and organic solvents under different pH values. However, it is difficult to obtain a product with up to 98% purity by this method. In fact, the purity obtained by this method is lower than that obtained by other methods. Additionally, the product has an undesirable color.

Therefore, there is an urgent need in the art for an improved method for purifying HMB that can simplify the process, reduce cost, and improve the quality of the product.

SUMMARY OF INVENTION

The present invention relates to a method for purification of HMB.

In one embodiment of the present invention, the method for purification of HMB comprises: (1) neutralizing crude HMB with a base to from crystals; (2) centrifuging the product; (3) drying the product to obtain a crystallized HMB salt; and (4) adding an inorganic acid to the product for dissolution and acidification. Finally, the HMB is extracted from the dissolved and acidified product to obtain high purity HMB.

In one preferred embodiment, the neutralizing reaction comprises dissolving the crude HMB and adding a base preferably at 20-60° C., and more preferably at 30-60° C. The base is added until the pH reaches 6-8. Diatomite is added and maintained at a temperature of 40-75° C., preferably at 45-75° C. The solution is filtered and the filtrate is recovered and slowly cooled to −10 to 20° C. to obtain the HMB crystal.

In another preferred embodiment, the crude HMB is dissolved in an aqueous solvent, which preferably is selected from the group consisting of, but not limited to: water and ethanol.

In another preferred embodiment, the dissolution and acidification step comprises adding the product containing the HMB salt into pure water in a weight ratio of 1:1-5 (HMB:water), more preferably in a weight ratio of 1:1-3, and then dropping an inorganic acid at 0-40° C., more preferably 10-40° C., into the solution until the pH reaches 1-3.5.

In another preferred embodiment, the base is a base, such as a divalent metal base, that can form an HMB salt having low solubility. Preferably the salt has a solubility of less than 50 percent, and most preferably the salt has a solubility lower than 10 percent. Preferably, the base is selected from the group consisting of, but not limited to, calcium hydroxide and magnesium hydroxide (the salt of β-hydroxyl-β-methyl butyrate thus obtained is, for example, calcium β-hydroxyl-β-methyl butyrate, and magnesium β-hydroxyl-β-methyl butyrate).

In another preferred embodiment, the inorganic acid is selected from the group consisting of, but not limited to, hydrochloric acid, sulfuric acid, nitric acid and phosphoric acid.

In another preferred embodiment, an organic solvent is used to extract HMB from the dissolved and acidified product to obtain an organic solvent extract. The organic solvent is then removed to produce high purity HMB.

In another preferred embodiment, the organic solvent is a water-immiscible solvent, and is selected from, but is not limited to: methyl acetate, ethyl acetate, butyl acetate, n-butanol, methyl ethyl ketone, methyl isobutyl ketone, dichloromethane, and dichloroethane.

In another preferred embodiment, the extraction includes repeating the extraction with the organic solvent two to five times with sufficiently stirring. The solution is left to stand and the organic phase is collected after each addition of the organic solvent.

In another preferred embodiment, the organic solvent is removed by vacuum distillation.

In another preferred embodiment, the organic solvent is ethyl acetate, and the organic solvent is removed by vacuum distillation under the following conditions: a distillation temperature of greater than or equal to 70° C. and vacuum of −0.09 Mpa or greater in the final stage. After the vacuum reaches −0.09 Mpa or more, the temperature reaches 60-70° C., and no bubbles are produced, distillation is complete.

In further embodiments, the method further comprises: reacting diacetone alcohol with hypochlorite before the neutralization step to produce a product containing an HMB salt and reacting the product containing the HMB salt with an inorganic acid to obtain a crude HMB product.

Other aspects of the present invention will be apparent to the skilled artisan in view of the disclosed contents in the present application.

The invention described herein relate generally to the field of chemical synthesis. Specifically, the present invention relates to a method for purification of β-hydroxyl-β-methyl butyrate.

After repeated and thorough study, the inventors unexpectedly found an ideal method for purifying 3-hydroxyl-β-methyl butyrate (HMB). The method comprises neutralizing a crude HMB with a base to obtain an HMB salt, cooling and crystallizing the salt solution, dissolving and acidifying the HMB salt crystals, and then extracting high purity HMB in a high purity. No extreme conditions, such as high temperature and high vacuum, are required in this method. In further exemplary embodiments, the method does not strain process equipment, and the process can be readily controlled and a can produce a high purity product.

According to at least one embodiment, the crude HMB is produced from the following chemical reactions. First, diacetone alcohol is reacted with hypochlorite to produce a sodium-HMB product. The sodium-HMB product is then reacted with an acid to obtain an aqueous solution of the sodium-HMB product. The aqueous solution is extracted by organic solvent several times and the organic phases are pooled. Finally, the solvents are removed under vacuum to produce crude HMB.

In the present invention, the crude HMB is reacted with a base to produce an HMB salt. The salt product is cooled, crystallized, dissolved, and acidified, and HMB of high purity is then extracted therefrom with good purity and mild process conditions.

In the preferred embodiment of the present invention, the organic solvent is removed by distillation under reduced pressure. The distillation temperature is controlled to remain less than 70° C. This method decreases loss of solvent and the organic solvent, such as ethyl acetate, can be removed by distillation as much as possible.

No strict conditions, such as high temperature and high vacuum, are required in the method of the present invention. Thus, according to certain embodiments, the present invention has a low impact or strain on process equipment. Additionally, the purification process can be readily controlled and a high purity product can be produced. The using the present method, the product exhibits favorable qualities including a colorless to light yellow appearance, a thick and transparent liquid, and a purity of 98 percent or greater.

According to at least one embodiment, the starting materials used in the present invention are commercially available materials known in the art. Preparation of the crude HMB is not specifically limited to the present embodiment, but instead may be carried out by a variety of methods that would be evident to one of skill in the art. Additionally, a person of ordinary skill would understand that a variety of known starting materials and operation conditions can be used in the present invention. It should be understood that no matter how the crude HMB is obtained, the process shall be contained within the protection scope of the present invention so long as it uses the purification method claimed herein.

The present invention will be further illustrated be making reference to the following specific examples. It should be understood that these examples are only for illustrating the present invention but should not be construed as limiting the scope of the present invention. The experimental methods used in the following examples are carried out according to the conventional conditions, or according to the conditions recommended by the manufacturer. Unless specifically indicated, the percentage and the part are calculated based on weight.

Unless otherwise defined, all technical and scientific terms used herein have the same meaning as commonly known by the skilled artisan. Additionally, any method and material similar to or equal to the contents as disclosed can be used in the present invention. The preferred embodiments and materials disclosed herein are merely for illustrative purposes.

EXAMPLE 1

Production of Crude HMB

1. Starting Materials and Auxiliary Materials

Starting materials and auxiliary materials used in the production of crude HMB are shown in Table 1.

TABLE 1

Starting and auxiliary materials for production of crude HMB

| Name of the starting and auxiliary materials | Quality | Ratio |
| --- | --- | --- |
| Hypochlorite | Industrial grade | 1000 kg |
| 4-Methyl-4-Hydroxyl-2-Pentanone (diacetone alcohol) | Industrial grade | reaction status dependent |
| Hydrochloric acid | Food grade | pH dependent |
| Ethyl acetate | Food grade | 1000 kg |

2. Operational Process and Processing Parameters 2.1 Oxidative Synthesis (it is a Strong Exothermic Reaction)

Sodium hypochlorite was pumped into a reaction kettle and diacetone alcohol (DIA) was slowly added. The addition velocity was controlled to maintain the reaction temperature of the materials in the kettle in the range of 10° to 20° C. during the course of the reaction. DIA was added until the addition significantly decreased the temperature of the kettle, indicating that the reaction was no longer taking place.

2.2 Acidification

The reaction product obtained through oxidative synthesis was pumped into another reaction kettle. The temperature was adjusted to about 20° C. Hydrochloric acid was added to adjust the pH to between 2 and 3.5. After the acid addition, the mixture was allowed to stand for 30 minutes. The chloroform by-product was removed from the bottom of the kettle.

2.3 Removal of Water by Evaporation

The reaction product obtained in by acidification was pumped into another reaction kettle and placed under vacuum until the volume of the product was reduced to approximately half of its initial volume. The product was cooled to about 60° C., discharged from the kettle, and filtered to remove the sodium chloride byproduct. The filtrates were combined and added to the reaction kettle.

2.4 Extraction

The filtrate was extracted by ethyl acetate three times. Before each extraction, the pH of the filtrate was adjusted to between 2 and 3.5 using hydrochloric acid. After each addition of ethyl acetate, the resultant mixture was thoroughly stirred and then allowed to stand and separate. The ethyl acetate layer was collected.

2.5 Removal of Ethyl Acetate

The extracted ethyl acetate layers were combined and pumped into a reaction kettle. Ethyl acetate was removed by vacuum distillation. The resultant product was cooled to less than 60° C. and discharged from the kettle to obtain the crude HMB.

EXAMPLE 2

Production of High Purity HMB

Starting auxiliary materials used for refining the crude HMB are shown in Table 2.

TABLE 2

Staring and auxiliary materials for HMB purification step

| Name of the starting and auxiliary materials | Quality | Addition amount (for each batch) |
|---|---|---|
| Crude HMB | Produced by the subject invention | 40 kg |
| Ethanol | Food grade | 200 kg |
| Calcium hydroxide | Food grade | pH dependent |
| Diatomite | Food grade | 2 kg |
| Hydrochloric acid | Food grade | pH dependent |
| Ethyl acetate | Food grade | 600 kg |

2. Operational Process and Processing Parameters 2.1 Neutralization and Crystallization Ethanol was added into a reaction kettle. The crude HMB prepared according to the method in Example 1 was added into the kettle, stirred, and heated within the range of 40 to 60° C. After the reaction was stable, calcium hydroxide was added to adjust the pH to between 6.5 and 7.5. Next, Diatomite was added at constant temperature. The reaction product was filtered into a crystallization kettle and slowly cooled to between 0 and 10° C.

2.2 Centrifugation

The reaction product obtained in the neutralization and crystallization step was added into a centrifuge having a laid filter cloth and centrifuged to obtain a wet product.

2.3 Drying

The wet product obtained from the centrifugation step was placed on a tray and put into an oven for drying at a temperature between 60 and 80° C. An HMB-Ca salt was obtained by drying drying. The drying step can be omitted if loss of solvent isn't acceptable.

2.4 Dissolution and Acidification

The HMB-Ca salt obtained in the dissolution and acidification step was weighed and pure water was added in a weight ratio of 3:1 (water:HMB-Ca). Hydrochloric acid was added at a temperature between 20 to 30° C. until the pH reached 2-3. The mixture was stirred to dissolve the HMB-Ca salt.

2.5 Extraction

The above dissolved and acidified solution was extracted by ethyl acetate three times. For each addition of ethyl acetate, the resultant mixture was thoroughly stirred and then allowed to stand and separate at 20~30° C. The ethyl acetate layers were collected.

2.6 Removal of Solvent

The extracts obtained from the extraction stage were combined. Ethyl acetate was removed by vacuum distillation. The distillation temperature was maintained between 40 and 70° C. and the vacuum was maintained at at least −0.09 Mpa. The vacuum pressure was maintained until the temperature reached between 65 and 70° C. and no bubbles were produced within the kettle. At this time, the distillation was stopped. The resultant high purity HMB was cooled to 50° C. and discharged from the kettle.

The product obtained through this process yielded HMB with a purity of 99.6 percent and a desirable color.

EXAMPLE 3

Alternate Production of High Purity HMB

The starting and auxiliary materials, operational process, and processing parameters used are the same as those used in Example 2, except that the neutralization and crystallization were carried out in the manner described below.

The crude HMB was pumped into a reaction kettle. Then, 120 kg of deionized water was added. Calcium hydroxide was added at a temperature between 30 and 50° C. to adjust the pH to between 6.5 and 7.5. Diatomite was added and the temperature was increased to between 65 and 70° C. and the temperature was maintained for 10 minutes. The reaction product was filtered to a reaction kettle and slowly cooled to between 0 and 10° C.

Centrifugation, drying, dissolution and acidification, extraction and removal of solvent were identical to the process described in Example 2. The product obtained through this process yielded HMB with a purity of 99.6 percent and a desirable color.

EXAMPLE 4

Study on Availability of Starting and Auxiliary Materials

Production was performed with materials, operational conditions, and processing parameters similar to those used in Example 2. Differences are listed in Table 3.

TABLE 3

Variations on HMB purity process

| Variation No. | Starting Materials | Process | Purity of HMB product |
|---|---|---|---|
| 1 | In step 2.1, calcium hydroxide was placed by magnesium hydroxide for neutralization | During neutralization, the pH was kept for 1.5 hours. Other processing conditions were the same as Example 2 | 99.2% |

TABLE 3-continued

Variations on HMB purity process

| Variation No. | Starting Materials | Process | Purity of HMB product |
|---|---|---|---|
| 2 | In Step 2.4, hydrochloric acid was replaced by sulfuric acid for acidification | Other processing conditions were the same as Example 2 | 99.5% |
| 3 | In Step 2.4, hydrochloric acid was replaced by nitric acid for acidification | Other processing conditions were the same as Example 2 | 98.8% |
| 4 | In Step 2.4, hydrochloric acid was replaced by phosphoric acid for acidification | Other processing conditions were the same as Example 2 | 98.7% |
| 5 | It step 2.5, ethyl acetate was replaced by methyl acetate for extraction | Other processing conditions were the same as Example 2 | 99.5% |
| 6 | It step 2.5, ethyl acetate was replaced by methyl ethyl ketone for extraction | Other processing conditions were the same as Example 2 | 99.2% |
| 7 | It step 2.5, ethyl acetate was replaced by methyl ethyl ketone for extraction | Other processing conditions were the same as Example 2, except that the posterior period of removal of solvent was maintained for 4 hours | 98.9% |
| 8 | It step 2.5, ethyl acetate was replaced by butyl acetate for extraction | Other processing conditions were the same as Example 2, except that the posterior period of removal of solvent was maintained for 4 hours | 99.3% |
| 9 | In step 2.5, n-butanol was used for extraction | Other processing conditions were the same as Example 2, except that the posterior period of removal of solvent was maintained for 4 hours | 99.4% |
| 10 | It step 2.5, ethyl acetate was replaced by iso-butanol for extraction | Other processing conditions were the same as Example 2, except that the posterior period of removal of solvent was maintained for 4 hours | 99.1% |
| 11 | In step 2.5, dichloromethane was used for extraction | Other processing conditions were the same as Example 2, except that the posterior period of removal of solvent was maintained for 4 hours | 98.4% |
| 12 | It step 2.5, ethyl acetate was replaced by dichloroethane for extraction | Other processing conditions were the same as Example 2, except that the posterior period of removal of solvent was maintained for 4 hours | 98.6% |

The contents of HMB in the final products were listed in Table 3. It can be found that products having high purity and excellent color could be obtained by suitable replacement of the starting materials.

All references cited in the subject invention are incorporated herein by reference, as each of the references is individually cited for reference. Additionally, it should be understood that various modifications or amendments could be made to the present invention by the skilled artisan after reading the above contents. All these equivalences fall within the scope as defined in the claims of the subject application.

The invention claimed is:

1. A method for purifying β-hydroxyl-β-methyl butyrate, comprising:
    (a) neutralizing a crude β-hydroxyl-β-methyl butyrate with a base;
    (b) crystallizing, centrifuging, and drying the crude β-hydroxyl-β-methyl butyrate to obtain a crystallized product containing a salt of β-hydroxyl-β-methyl butyrate;
    (c) adding an inorganic acid to the salt of β-hydroxyl-β-methyl butyrate product for dissolution and acidification; and
    (d) extracting β-hydroxyl-β-methyl butyrate from the dissolved and acidified salt of β-hydroxyl-β-methyl butyrate to obtain β-hydroxyl-β-methyl butyrate;
    wherein the purity of the β-hydroxyl-β-methyl butyrate is about 97 percent or greater.

2. The method of claim 1, wherein in step (a), the neutralizing comprises:
    (a) dissolving the crude β-hydroxyl-β-methyl butyrate;
    (b) adding a base at 20-60° C. until the pH reaches 6-8;
    (c) adding diatomite and maintaining the temperature at 40-75° C.;
    (d) filtering and recovering a filtrate; and
    (e) slowly cooling the filtrate to −10 to 20° C. to obtain a β-hydroxyl-β-methyl butyrate crystal.

3. The method of claim 2, wherein the crude β-hydroxyl-β-methyl butyrate is dissolved in an aqueous solvent.

4. The method of claim 1, wherein in step (c), the dissolution and acidification comprises:
    (a) adding the salt of β-hydroxyl-β-methyl butyrate product into pure water in a weight ratio of 1:1-5; and
    (b) dropping an inorganic acid at 0-40° C. until the pH reaches 1-3.5.

5. The method of claim 1, wherein the base is a metal salt having low solubility.

6. The method of claim 1, wherein the inorganic acid is selected from the group consisting of hydrochloric acid, sulfuric acid, nitric acid and phosphoric acid.

7. The method of claim 1, wherein in step (c), an organic solvent is used to extract β-hydroxyl-β-methyl butyrate from the dissolved and acidified product to obtain an organic solvent extract, and further wherein the organic solvent is removed to produce β-hydroxyl-β-methyl butyrate of high purity.

8. The method of claim 7, wherein the organic solvent is a water-immiscible solvent, selected from the group consisting of: methyl acetate, ethyl acetate, butyl acetate, n-butanol, methyl ethyl ketone, methyl isobutyl ketone, dichloromethane, and dichloroethane.

9. The method of claim 7, wherein the organic solvent is removed by vacuum distillation.

10. The method of claim 1, wherein before step (a), the method further comprises:
    (a) reacting diacetone alcohol with hypochlorite to produce a product containing a salt of β-hydroxyl-β-methyl butyrate;
    (b) reacting the product containing the salt of β-hydroxyl-β-methyl butyrate obtained in step (a) with an inorganic acid to obtain a crude β-hydroxyl-β-methyl butyrate.

11. The method of claim 3, wherein the aqueous solvent is selected from the group consisting of water and ethanol.

12. The method of claim 5 wherein, the base is selected from the group consisting of calcium hydroxide and magnesium hydroxide.

13. The method of claim 1, wherein the method has less strain on equipment when compared to conventional production methods.

* * * * *